(12) United States Patent
Li et al.

(10) Patent No.: US 9,001,324 B2
(45) Date of Patent: Apr. 7, 2015

(54) OPTICAL FIBER SURFACE ENHANCED RAMAN SPECTROSCOPY (SERS) PROBE

(75) Inventors: Zhiyong Li, Redwood City, CA (US); Min Hu, Sunnyvale, CA (US); Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 44 days.

(21) Appl. No.: 13/810,982

(22) PCT Filed: Jul. 30, 2010

(86) PCT No.: PCT/US2010/044039
§ 371 (c)(1),
(2), (4) Date: Jan. 18, 2013

(87) PCT Pub. No.: WO2012/015443
PCT Pub. Date: Feb. 2, 2012

(65) Prior Publication Data
US 2013/0120748 A1 May 16, 2013

(51) Int. Cl.
*G01J 3/44* (2006.01)
*G01N 21/65* (2006.01)

(52) U.S. Cl.
CPC .................... *G01N 21/658* (2013.01)

(58) Field of Classification Search
CPC ............... G01N 21/65; G01N 21/658; G01N 2021/656; G01J 3/44; G01J 3/02
USPC ............................................. 356/301; 385/77
See application file for complete search history.

(56) References Cited

U.S. PATENT DOCUMENTS

| 5,677,196 | A  | 10/1997 | Herron et al. |
| 6,193,870 | B1 | 2/2001  | Morse et al.  |
| 6,222,619 | B1 | 4/2001  | Herron et al. |
| 6,756,795 | B2 | 6/2004  | Hunt et al.   |
| 6,777,244 | B2 | 8/2004  | Pepper et al. |

(Continued)

FOREIGN PATENT DOCUMENTS

| CN | 1659425    | 8/2005 |
| CN | 101529229 A | 9/2009 |

(Continued)

OTHER PUBLICATIONS

Baldwin, Jean, Norbert Schuhler, Ian S. Butler, & Mark P. aNDREWS, "Integrated Optics Evanescent Wave Surface Enhanced Raman Scattering (IO-EWSERS) of Mercaptopyridines on a Planar Optical Chemical Bench: Binding of Hydrogen and Copper Ion", Langmuir, 1996, vol. 12, pp. 6389-6398.

(Continued)

*Primary Examiner* — Tarifur Chowdhury
*Assistant Examiner* — Md Rahman
(74) *Attorney, Agent, or Firm* — North Shore Associates

(57) ABSTRACT

A surface enhanced Raman spectroscopy (SERS) probe apparatus and a method of SERS probing employ Raman-active surfaces of a plurality of nanoscale field concentrator (NFC) structures at a terminal end of an optical fiber. The SERS probe apparatus includes an optical fiber having an optical path and a terminal end that terminates the optical path. The SERS probe apparatus further includes a plurality of NFC structures and nanoparticles on surfaces of the plurality of NFC structures. First ends of the NFC structures are adjacent to the terminal end of optical fiber. The nanoparticles are Raman active to an analyte.

15 Claims, 6 Drawing Sheets

(56) References Cited

U.S. PATENT DOCUMENTS

| | | |
|---|---|---|
| 7,158,219 B2 | 1/2007 | Li et al. |
| 7,236,242 B2 | 6/2007 | Kamins et al. |
| 7,245,370 B2 | 7/2007 | Bratkovski et al. |
| 7,256,886 B2 | 8/2007 | Cullum et al. |
| 7,342,656 B2 | 3/2008 | Islam et al. |
| 7,388,661 B2 | 6/2008 | Li et al. |
| 7,402,531 B1 | 7/2008 | Kuekes et al. |
| 7,463,661 B2 | 12/2008 | Ogura |
| 7,483,130 B2 | 1/2009 | Baumberg et al. |
| 7,528,948 B2 | 5/2009 | Bratkovski et al. |
| 7,583,379 B2 | 9/2009 | Zhao et al. |
| 7,597,814 B2 | 10/2009 | Stasiak et al. |
| 7,656,525 B2 | 2/2010 | Zhao et al. |
| 7,667,238 B2 | 2/2010 | Erchak |
| 7,833,842 B2 | 11/2010 | Williams |
| 7,898,658 B2 | 3/2011 | Moskovits |
| 7,960,251 B2 | 6/2011 | Choi et al. |
| 8,108,943 B2 | 1/2012 | Anderson |
| 8,148,294 B2 | 4/2012 | Wang et al. |
| 8,149,397 B2 | 4/2012 | Lee et al. |
| 8,154,722 B2 | 4/2012 | Yamada et al. |
| 8,184,284 B2 | 5/2012 | Ebstein |
| 8,279,435 B2 | 10/2012 | Wang et al. |
| 8,358,408 B2 * | 1/2013 | Wu et al. ............. 356/301 |
| 2002/0180306 A1 | 12/2002 | Hunt |
| 2003/0059820 A1 * | 3/2003 | Vo-Dinh ............. 435/6 |
| 2003/0077023 A1 | 4/2003 | Troll |
| 2006/0017917 A1 * | 1/2006 | Cullum et al. ............. 356/301 |
| 2006/0038990 A1 | 2/2006 | Habib et al. |
| 2006/0119843 A1 * | 6/2006 | O'Connell ............. 356/246 |
| 2006/0119853 A1 | 6/2006 | Baumberg |
| 2006/0231381 A1 | 10/2006 | Jensen |
| 2006/0252065 A1 | 11/2006 | Zhao et al. |
| 2007/0070341 A1 | 3/2007 | Wang |
| 2007/0086001 A1 | 4/2007 | Islam et al. |
| 2007/0127164 A1 | 6/2007 | Ofek |
| 2007/0252982 A1 | 11/2007 | Wang |
| 2008/0017845 A1 | 1/2008 | Drndic |
| 2008/0024776 A1 | 1/2008 | Bratkovski et al. |
| 2008/0080816 A1 * | 4/2008 | D'Urso et al. ............. 385/77 |
| 2008/0094621 A1 * | 4/2008 | Li et al. ............. 356/301 |
| 2008/0144026 A1 | 6/2008 | Zhao et al. |
| 2008/0166706 A1 | 7/2008 | Zhang et al. |
| 2008/0174775 A1 | 7/2008 | Moskovits et al. |
| 2008/0187648 A1 | 8/2008 | Hart |
| 2008/0311028 A1 | 12/2008 | Stanbery |
| 2009/0261815 A1 | 10/2009 | Cairns |
| 2009/0303472 A1 | 12/2009 | Zhao et al. |
| 2010/0303722 A1 | 12/2010 | Jin et al. |
| 2010/0321684 A1 | 12/2010 | Bratkovski et al. |
| 2011/0001118 A1 | 1/2011 | Bhupendra |
| 2011/0030792 A1 | 2/2011 | Miguez |
| 2011/0128537 A1 | 6/2011 | Bond et al. |
| 2011/0188034 A1 | 8/2011 | Stuke et al. |
| 2012/0107948 A1 | 5/2012 | Li et al. |
| 2012/0119315 A1 | 5/2012 | Ou et al. |
| 2012/0188540 A1 | 7/2012 | Bratkovski et al. |
| 2012/0212732 A1 | 8/2012 | Santori et al. |
| 2012/0212733 A1 | 8/2012 | Kodali et al. |

FOREIGN PATENT DOCUMENTS

| | | |
|---|---|---|
| CN | 101688809 A | 3/2010 |
| EP | 1426756 | 6/2004 |
| EP | 2058908 | 5/2009 |
| JP | 2000-206048 | 7/2000 |
| JP | 2004-184414 | 2/2004 |
| JP | 2006145230 | 6/2006 |
| JP | 2009-515543 | 4/2009 |
| JP | 2009-544967 | 12/2009 |
| WO | WO-03083480 | 10/2003 |
| WO | WO-2008013683 | 1/2008 |
| WO | WO-2010088585 | 8/2010 |
| WO | WO-2010126640 | 11/2010 |
| WO | WO-2011133143 | 10/2011 |
| WO | WO-2011133144 | 10/2011 |

OTHER PUBLICATIONS

Gopinath, Ashwin, et al., Deterministic Aperiodic Arrays of Metal Nanoparticles for Surface-enhanced Raman Scattering (SERS), Publication Date: Mar. 2, 2009; vol.: 17; on pp.: 3741-3753. < http://wwwbio-page.org/boriskina/Boriskina_OE2009.pdf >.

Giglmayr, Josef, "Nano-Finger Electrodes for the Electro-Optical Generation and Tuning of Gratings at Several Wavelengths", < http://www.ipme.ru/ipme/conf/NN2003_Abstrac.

Krishnamoorthy, Sivashankar, et al., Combining Micelle Self-assembly with Nanostencil Lithography to Create Periodic/aperiodic Micro-/nanopatterns on Surfaces, Publication Date: Jul. 30, 2008; vol.: 20; On pp.: 3533-3538. < http://onlinelibrary.wiley.com/doi/10.1002/adma.200702478/abstract >.

Chen, S.Y. et al., Raman Antenna Formed by Molecule/plasmonic Nanostructure Hybrid System, (Research Paper), Conference Paper, Quantum Electronics and Laser Science Conference, May 1, 2011, Baltimore, Maryland.

Du, Y. et al., SERS Enhancement1 Dependence on the Diameter and Aspect Ratio of Silver-nanowire Array Fabricated by Anodic Aluminium Oxide Template, (Research Paper), Applied Surface Science, Dec. 30, 2008, pp. 1901-1905, vol. 255, No. 5.

Weng, T.W. et al., Area Effect of Patterned Carbon Nanotube Bundle on Field Electron Emission Characteristics, (Research Paper), 9th International Conference on Atomically Controlled Surfaces, Interfaces and Nanostructures 2007, Sep. 30, 2008, pp. 7755-7758, vol. 254, No. 23.

Cubukcu, E., et al., "Plasmonic Laser Antennas and Related Devices", IEEE Journal of Selected Topics in Quantum Electronics, Nov./Dec. 2008, vol. 14, No. 6, pp. 148-1461.

Fan et al., "Multilayer Silver Nanoparticles Modified Optical Fiber Tip for High Performance SERS Remote Sensing," 217th ECS Meeting—Vancouver, Canada, Apr. 25-Apr. 30, 2010, J2-Electrochemical Nano/Bio Sensors 2, Abs# 1830.

Fan, J. G. et al., "Integrating Aligned Nanorod Array onto Optical Fibers for SERS Probes," Proc. of SPIE—Nanoengineering: Fabrication, Properties, Optics, and Devices III, vol. 6327, 2006, pp. R-1 to R10.

Guieu, Valérie, et al. "Multitip-localized enhanced Raman scattering from a nanostructured optical fiber array." The Journal of Physical Chemistry C 113.3 (2008): 874-881.

International Search Report, Mar. 30, 2011, PCT Application No. PCT/US2010/044039, Filed Jul. 30, 2010.

Lucotti et al., "Fiber-optic SERS sensor with optimized geometry," Elsevier, ScienceDirect, Sensors and Actuators B, vol. 121, 2007, 356-364.

PCT International Search Report, Jan. 20, 2011, Hewlett-Packard Development Company, L.P. (PCT/US2010/031790, Filed Apr. 20, 2010).

PCT International Search Report, Dec. 23, 2010, Hewlett-Packard development Company, L.P. (PCT/US2010/031809, Filed Apr. 20, 2010).

Ren, Hongliang, et al. "The preparation of optical fibre nanoprobe and its application in spectral detection." Optics & Laser Technology 39.5 (2007): 1025-1029.

Segawa, H., et al., "Top-gathering pillar array of hybrid organic-inorganic material by means of self-organization", Applied Physics A—Materials Science & Processing, Mar. 17, 2006, vol. 83, pp. 447-451.

White, Daniel J., et al. "Nanostructured optical fibre for surface-enhanced Raman scattering sensing." Proc SPIE. vol. 7102. 2008.

Xie et al., "Polymer optical fiber SERS sensor with gold nanorods," Elsevier, Optics Communications, vol. 282, 2009, pp. 439-442.

Zhang et al., "Single-Fiber Probe Based on Surface Enhanced Raman Scattering (SERS)," IEEE Sensors, 2005, pp. 1088-1091.

Qui et al: "Surface-enhanced Raman characteristics of Ag cap aggregates on silicon nanowire arrays", Nanotechnology, IOP, Bristol, GB, vol. 17, No. 23, Dec. 14, 2006.

* cited by examiner

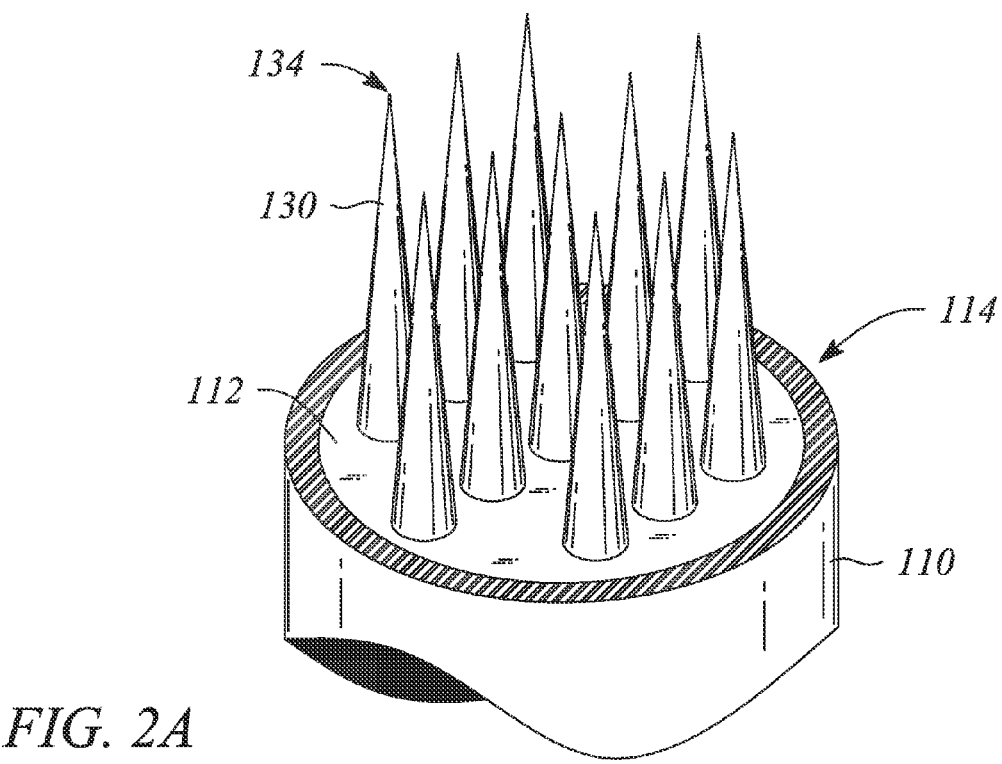
FIG. 2A
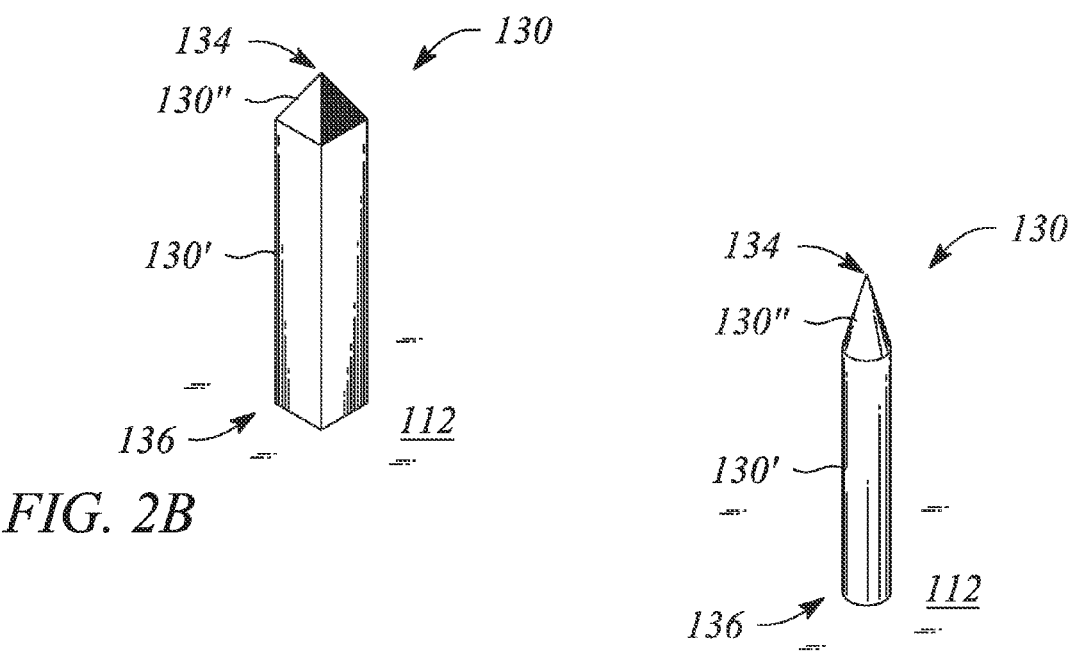
FIG. 2B
FIG. 2C

OPTICAL FIBER SURFACE ENHANCED RAMAN SPECTROSCOPY (SERS) PROBE

CROSS-REFERENCE TO RELATED APPLICATIONS

N/A

STATEMENT REGARDING FEDERALLY SPONSORED RESEARCH OR DEVELOPMENT

N/A

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that result when the material is illuminated by a form of electromagnetic radiation (e.g., visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman-scattering.

Raman-scattering optical spectroscopy employs an emission spectrum or spectral components thereof produced by inelastic scattering of photons by an internal structure of the material being illuminated. These spectral components contained in a response signal (e.g., a Raman signal) may facilitate determination of the material characteristics of an analyte species including identification of the analyte.

Unfortunately, the Raman signal produced by Raman-scattering is extremely weak in many instances compared to elastic or Rayleigh scattering from an analyte species. The Raman signal level or strength may be significantly enhanced by using a Raman-active material (e.g., Raman-active surface), however. For example, a surface that includes a Raman-active material may be employed in surface enhanced Raman-scattering (SERS) optical spectroscopy to significantly enhance a signal level or intensity of the Raman signal produced by a particular analyte species. While SERS has proven to yield good results in many applications, further improvements are still being sought.

For example, SERS often suffers from or exhibits unpredictable hot spots across the surface. The hot spots produce much higher-level Raman signals than surrounding areas but the location and quantity of these hot spots can be difficult to control. As such, it is often necessary to flood the entire surface with analyte to insure that sufficient analyte reaches the hot spots and produces a detectable Raman signal. Requiring the surface to be flooded precludes detection of very small amounts of analyte (e.g., single molecules) and also hinders identifying other analyte characteristics such as species distribution within a sample.

Attempts to localize or control the production of hot spots have included the use of sharp tips in conjunction with a SERS surface in what is known as tip enhanced Raman spectroscopy (TERS). In TERS, a sharp, conductive tip is placed very close to but spaced apart from the SERS surface. The tip acts as an antenna concentrating and locally enhancing the electromagnetic field in a region between the tip and the surface. While producing results including detection of extremely small quantities of analyte, TERS presents many practical challenges to implementation and use. In addition, SERS can present a problem when dealing with analytes that must be or at least are better accessed remotely.

BRIEF DESCRIPTION OF THE DRAWINGS

The various features of examples may be more readily understood with reference to the following detailed description taken in conjunction with the accompanying drawings, where like reference numerals designate like structural elements, and in which:

FIG. 2A illustrates a perspective view of a plurality of positive nanoscale field concentrator (NFC) structures, according to an example.

FIG. 2B illustrates a perspective view of a columnar-shaped positive NFC structure, according to an example.

FIG. 2C illustrates a perspective view of a columnar-shaped NFC structure, according to another example.

Figure 1A:
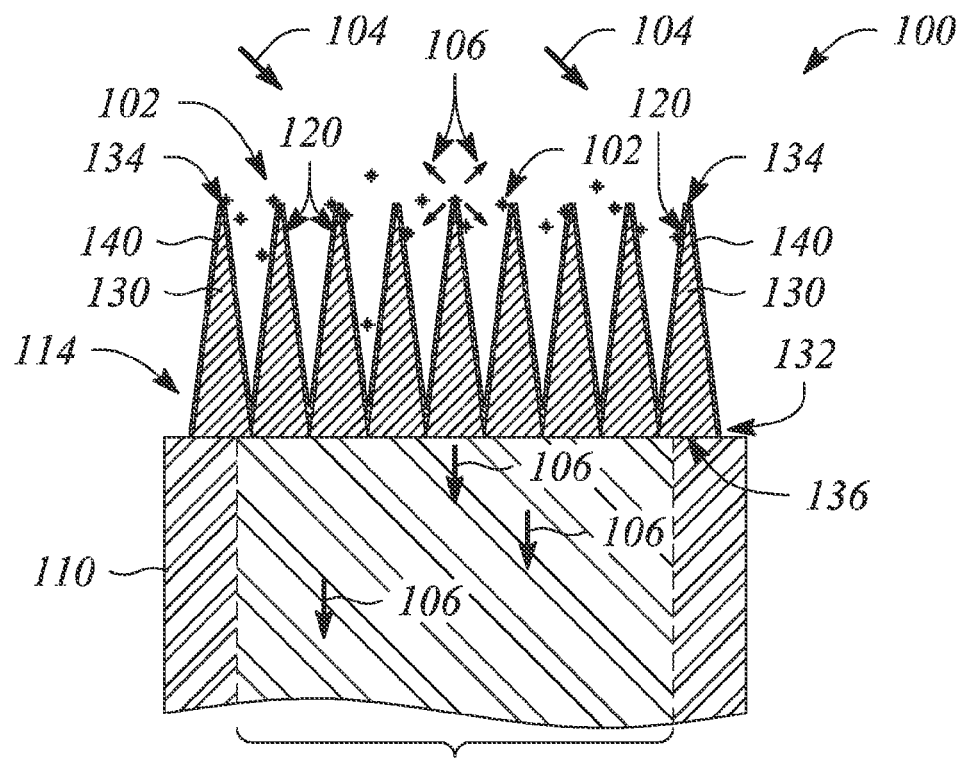
FIG. 1A illustrates a cross sectional view of a surface enhanced Raman spectroscopy (SERS) probe apparatus, according to an example.

Certain examples have other features that are one of in addition to and in lieu of the features illustrated in the above-referenced figures. These and other features are detailed below with reference to the preceding drawings.

DETAILED DESCRIPTION

Embodiments provide surface enhanced Raman spectroscopy (SERS). In particular, SERS is performed on or in a vicinity of a tip of a nanoscale field concentrator (NFC) structure, according to some examples. The NFC structure is a member of a plurality of NFC structures that are located adjacent to, and in some examples, on a terminal end of an optical fiber (e.g., a fiber optic transmission line). The terminal end terminates an optical path of the optical fiber. The tip of the NFC structure is configured to enhance or concentrate an optical field in a vicinity of the tip. The concentrated optical field, in turn, may enhance a signal strength of a Raman signal produced by Raman scattering from an analyte. In some examples, the analyte is adsorbed on the NFC structure tip, or a surface thereof, and the enhanced the Raman signal is a result Raman scattering by the adsorbed analyte. Further according to some examples, the Raman signal may be collected and subsequently guided or transported away from the NFC structure at the terminal end via the optical path of the optical fiber. The collection and transport of the Raman signal by the optical fiber may improve detection of the Raman signal (e.g., improve a signal-to-noise ratio of the Raman signal). Moreover, by locating the NFC structures at the terminal end of the optical fiber, SERS analysis of analytes may be facilitated by enabling the SERS to be performed remotely from one or both of an illumination source and a detector used to receive the Raman signal.

A 'nanoscale field concentrator (NFC) structure' is defined herein as a nanoscale structure comprising one or more nanoscale components or elements that act either singly or in concert to concentrate or enhance an electromagnetic field (e.g., an optical field of an illumination source) in a vicinity of the tip of the NFC structure. According to the definition, the NFC structure may comprise a nanocone or a related nanostructure having a relatively sharp tip in some examples. The sharp tip interacts with an incident electromagnetic field to concentrate the field in a vicinity of the tip. Other sharp tipped nanoscale structures, such as but not limited to, nano-columns and nanowires with sharpened ends are also NFC structures, by definition herein.

According to the definition, in other examples the NFC structure may comprise a grouping of two or more nano-columns or nanofingers. The nanofingers of the grouping angle toward but do not touch one another in a vicinity of the tip of the NFC structure such that a small, nanoscale gap exists between respective ends of the nanofingers in the grouping. The small gap enhances or concentrates an incident electromagnetic field.

According to the definition, in yet other examples the NFC structure may comprise two or more adjacent, generally elongated (e.g., columnar or conical) nanostructures, each elongated nanostructure having a cap at an end corresponding to the tip of the NFC structure. The cap is generally larger in cross section than the elongated nanostructure. In some examples, the cap may have a generally flattened, disk-like shape. As such, the capped elongated nanostructure may be referred to as a 'mushroom structure' owing to its resemblance to a mushroom. In another example, the cap may have a more rounded shape such as, but not limited to, that of a spheroid. In yet other examples, the cap may be generally cylindrical, be faceted, or even rectilinear in shape. The caps of adjacent elongated nanostructures are separated from one another by a nanoscale gap. The gap between adjacent caps enhances the incident electromagnetic field. In some examples, the cap is metallic and comprises a metal. In some examples, the metallic cap may take the place of or be equivalent to nanoparticles on a surface of the NFC structure that are described in more detail below.

In various examples, an element or elements of the NFC structure (e.g., the nanocone or related structure, the nanofingers of the grouping, and the elongated nanostructure with the cap) generally comprise an elongated, nanoscale structure having a length that exceeds by more than several times a nanoscale cross sectional dimension (e.g., width) taken in a plane perpendicular to the length (e.g., length>2×width). In some examples, the length of the element(s) of the NFC structure is much greater than the width or cross sectional dimension. In some examples, the length (or height) exceeds the cross sectional dimension (or width) by more than a factor of 5 or 10. For example, the width of the NFC structure element may be about 40 nanometers (nm) and the height may be about 400 nm. In another example, the width at a base of the NFC structure may be between 20 nm and 100 nm and the length may be more than about 1 micrometer (μm). In another example, the NFC structure element may be conical with a base having a width of between 100 nm and 500 nm and a length or height that is between one and several micrometers. In other examples, the length is less than the width or cross sectional dimension. In yet other examples, the length and width are about equal.

In various examples, the NFC structures may be one or more of produced by an additive process (e.g., grown or printed), formed by an imprinting or molding process (e.g., nanoimprint lithography) and produced by a subtractive process (e.g. etching). For example, the NFC structures may be grown using a vapor-liquid-solid (VLS) growth process. In another example, the NFC structures may be produced using an etching process such as, but not limited to, wet etching and reactive ion etching, to remove surrounding material leaving behind the NFC structures. In another example, nanoimprint lithography may be used. Various techniques used in the fabrication of micro-electromechanical systems (MEMS) and nano-electromechanical systems (NEMS) are applicable to the fabrication of the NFC structures.

By definition herein, 'nanoscale' means a dimension that is generally less than about 1000 nanometers (nm). For example, a structure that is about 5-100 nm in extent is considered a nanoscale structure. Further, as used herein, the article 'a' is intended to have its ordinary meaning in the patent arts, namely 'one or more'. For example, 'a NFC structure' means one or more NFC structures and as such, 'the NFC structure' explicitly means 'the NFC structure(s)' herein. Also, any reference herein to 'top', 'bottom', 'upper', 'lower', 'up', 'down', 'front', 'back', 'left' or 'right' is not intended to be a limitation herein. Herein, the term 'about' when applied to a value generally means plus or minus 10% unless otherwise expressly specified. Moreover, examples herein are intended to be illustrative only and are presented for discussion purposes and not by way of limitation.

Figure 1B:
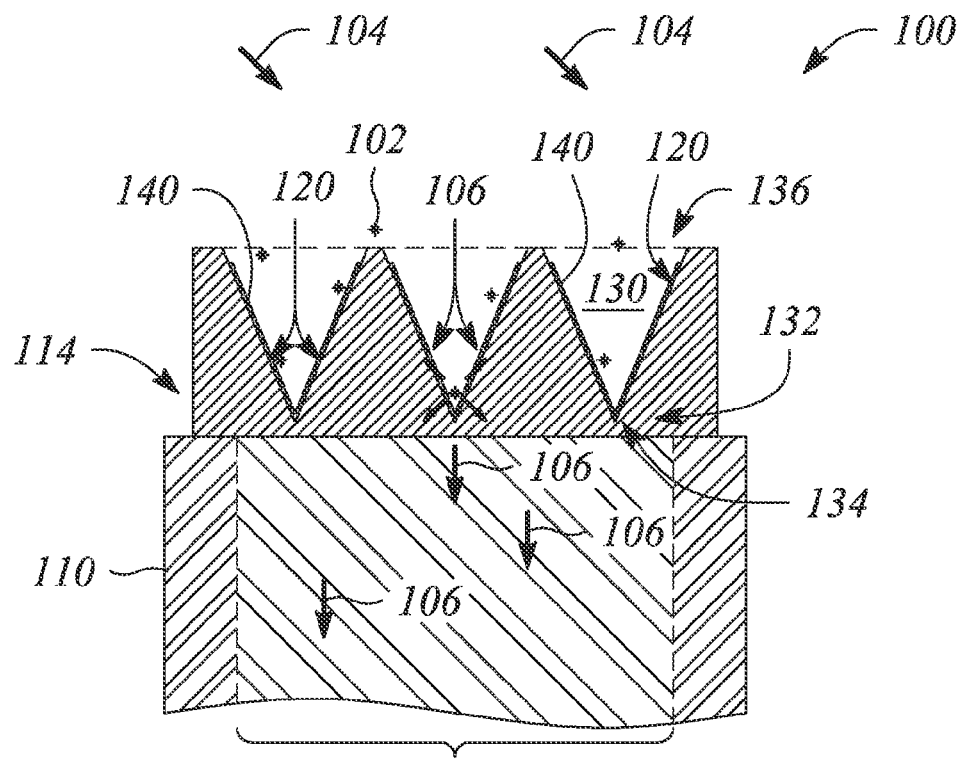
FIG. 1B illustrates a cross sectional view of a surface enhanced Raman spectroscopy (SERS) probe apparatus, according to another example.

FIG. 1A illustrates a cross sectional view of a surface enhanced Raman spectroscopy (SERS) probe apparatus 100, according to an example. FIG. 1B illustrates a cross sectional view of a surface enhanced Raman spectroscopy (SERS) probe apparatus 100, according to another example. An analyte 102 may be introduced to and analyzed using the SERS apparatus 100, according to some examples. For example, the analyte 102 may be introduced by inserting the SERS probe apparatus 100 into an area containing the analyte 102. In another example, a material (e.g., a gas or a liquid) containing the analyte 102 may be flowed past the SERS probe apparatus 100 to introduce the analyte 102 to the SERS probe apparatus 100 for the analysis of the analyte 102. In some examples, the analyte 102 is adsorbed onto a surface of the SERS probe apparatus 100. The analyte 102 is illuminated by illumination signal 104 to produce a Raman signal 106. The Raman signal 106 is produced by the analyte 102 through surface enhanced Raman scattering, according to some examples. The Raman signal 106 produced by the analyte 102 is detected and analyzed to facilitate analysis (e.g., identification) of the analyte 102, according to some examples. The illumination signal 104 and Raman signal 106 are illustrated as arrows indicating a principal direction of propagation thereof, by way of example.

As illustrated in FIGS. 1A and 1B, the SERS probe apparatus 100 comprises an optical fiber 110. In some examples, the optical fiber 110 comprises a multi-mode optical fiber. For example, the optical fiber 110 may be a plastic or polymer optical fiber (POF). A POF may comprise a poly methyl methacrylate (PMMA) or acrylic core with a fluorinated polymer (e.g., silicone resin) cladding, for example. Other materials such as, but not limited to, cyclic transparent optical polymer (CYTOP), polystyrene, polycarbonate and related plastics may also be used for optical fiber cores in a multi-mode optical fiber. In other examples, the optical fiber 110 comprises a single mode optical fiber. For example, the single-mode optical fiber may comprise silica glass or various other glass materials. Various optically transparent crystalline materials may also be employed to realize a single-mode optical fiber, for example.

The optical fiber 110 has an optical path 112 that extends parallel to a longitudinal axis of the optical fiber 110 and a terminal end 114. The terminal end 114 terminates the optical path 112. By definition herein, the terminal end 114 has an interface surface or boundary (e.g., an interface plane) that intersects and substantially 'cuts through' the optical path, or a central axis thereof, in such a way that the optical path 112 of the optical fiber 110 is terminated at (i.e., does not continue beyond) the terminal end 114. Light propagating in the optical path 112 toward the terminal end 114 either may exit the optical fiber 110 at the terminal end 114 or may be reflected back into the optical fiber 110 by the terminal end 114 (e.g., ignoring absorption by materials of the terminal end 114).

The terminal end 114 (e.g., interface surface thereof) may be substantially perpendicular to the optical path 112, for example. In another example, the terminal end 114 may cut through the optical path 112 of the optical fiber 110 at an acute angle. In another example, the terminal end 114 may be characterized by a curved interface boundary or surface (e.g., a lens shape) that terminates the optical path 112. In yet other examples, the terminal end 114 may have one or more of a faceted shape, a compound curvilinear shape and an irregular shape. The terminal end 114 of the optical fiber 110 illustrated in FIGS. 1A and 1B are examples of terminal end 114 characterized by an interface surface that is substantially perpendicular to the optical path 112. The example interface surfaces of the terminal ends 114 in FIGS. 1A and 1B are illustrated for discussion and not by way of limitation.

The SERS probe apparatus 100 further comprises surfaces 120 of a plurality of nanoscale field concentrator (NFC) structures 130. In particular, the surfaces 120 of the NFC structures 130 establish an overall shape and extent of the NFC structures 130 by defining a boundary between the NFC structures 130 and a surrounding medium. First ends 132 of the NFC structures 130 are adjacent to the terminal end 114 of the optical fiber 110, for example in either direct contact or indirect contact with the interface surface of the terminal end, depending on the example. For example, as illustrated in FIG. 1A, the NFC structures 130 are attached to (e.g., in direct contact with) a material of the optical fiber 110 at the interface surface of the terminal end 114 of the optical fiber 110. The NFC structures 130 may be rigidly attached to the terminal end 114, for example. FIGS. 1A and 1B illustrate the NFC structures 130 as nanocones by way example and not limitation. In some examples, the plurality of NFC structures 130 is arranged in a periodic array while in other examples an aperiodic array or arrangement may be employed.

In some examples, the NFC structures 130 of the plurality are 'positive' NFC structures. By definition, a 'positive' NFC structure is a NFC structure that is formed from and is substantially filled with a relatively solid or rigid material of the NFC structure 130. As such, the surface 120 of the positive NFC structure 130 is on an outside of the NFC structure 130 and the NFC structure shape defined by the surface 120 is substantially filled with NFC structure material of the positive NFC structure 130. FIG. 1A illustrates a cross sectional view of a plurality of positive NFC structures 130 (e.g., nanocones), for example.

In other examples, the NFC structures 130 of the plurality are 'negative' NFC structures. A 'negative' NFC structure, by definition herein, is an inverse NFC structure or an NFC structure-shaped cavity in a material surrounding the cavity. For example, the negative NFC structures 130 are cavities formed in a support material (e.g., by nanoimprint lithography). The cavities may be filled with a material such as a gas or a liquid. The surrounding material that defines the shape of the negative NFC structures 130 provides the surface 120 of the negative NFC structure 130 (i.e., provides the cavity wall). FIG. 1B illustrates a cross sectional view of a plurality of negative NFC structures 130 that are substantially hollow nanocone-shaped cavities, for example. As illustrated, the example negative NFC structures 130 are substantially filled with air and the surfaces 120 are on a surface of a support material (e.g., PMMA) defining the plurality of negative NFC structures 130.

Both of the positive NFC structures 130 and the negative NFC structures 130 of the plurality comprise a tip 134 at one end and a base 136 at an end 132 that is opposite the tip 134. According to some examples, the tip 134 is substantially sharp. By 'sharp' it is meant that the tip 134 tapers to a point at an end that forms or provides the tip 134. The edge or the point generally has or is characterized by a relatively acute angle of inflection between surfaces 120 of the NFC structures 130 in a vicinity of the tip 134 leading up to the edge or the point. In other words, a cross sectional size in a vicinity of the tip 134 (i.e., the edge or the point) is much smaller than an overall cross sectional size of the NFC structure 130 away from the tip 134. In particular, the cross sectional size of the NFC structure 130 tip 134 is substantially smaller than a cross sectional size of the base 136 of the NFC structure 130. As such, the NFC structure 130 having a tip 134 that is substantially sharp, as described herein, distinguishes the NFC structure 130 from other nanostructures, such as nano-needles, nanorods, nanowires or related nanostructures having a generally rounded or flattened tip. Herein, the 'first end' 132 of a NFC structure 130 is the end closest to the interface surface of the terminal end 114 of the optical fiber 110. For a positive NFC structure 130, the first end 132 is the base 136, while the first end 132 of a negative NFC structure 130 is the tip 134 (i.e., the inverse of the positive NFC structure).

In some examples, the NFC structures 130, whether a positive NFC structure or a negative NFC structure, have a generally tapered shape as illustrated in FIGS. 1A and 1B. In some examples, the tapered shape of the NFC structure 130 is conical comprising a generally circular cross sectional shape, the cross section being defined in a plane that is substantially perpendicular to a long axis of the NFC structure 130. In other examples (not illustrated), the tapered shape of the NFC structures 130 may be generally faceted or pyramidal, for example having three, four, or more facets or sides. In yet other examples, the tapered shape may have a curvilinear perimeter when considering a cross section perpendicular to the long axis of the NFC structure 130. FIG. 2A illustrates a perspective view of a plurality of positive NFC structures 130, according to an example. As illustrated, the plurality of positive NFC structures 130 are on a terminal end 114 of an optical fiber 110 within a region of the terminal end corresponding to the optical path 112. The illustrated NFC structures 130 have a generally tapered, conical shape and may be referred to as nanocones.

In other examples, the NFC structures 130, whether a positive NFC structure or a negative NFC structure, has a columnar shaped portion. In such examples, the NFC structure 130 comprises columnar portion that extends from the point of attachment to a vicinity of the tip 134 and a tapered portion at or in the vicinity of the tip 134. The tapered portion provides the substantially sharp tip 134. In particular, the NFC structure 130 having a columnar shape tapers to a substantially sharp point only in a vicinity of the tip 134 to distinguish from the tapered-shape NFC structure 130 of FIG. 2A. The columnar portion may have either curvilinear or faceted perimeter in cross section. In particular, with respect to a cross section taken in a plane perpendicular to the long axis of the NFC structure 130 and within the columnar portion, the columnar-shaped NFC structure 130 may have a cross section that is characterized by either a curvilinear perimeter or a polygonal perimeter. For example, the columnar-portion may have a triangular cross section, a rectangular cross section or a cross section with more than four sides. In another example, the columnar portion may have a perimeter that is circular, oval or similarly curvilinear (e.g., a square with rounded corners).

FIG. 2B illustrates a perspective view of a columnar-shaped positive NFC structure 130, according to an example. A columnar portion 130' of the columnar-shaped NFC structure 130 extends from the base 136 to near the tip 134. In the vicinity of the tip 134, the columnar portion 130' is replaced by or gives way to the tapered portion 130", as illustrated. Further as illustrated, the columnar-shaped NFC structure 130 has a rectangular cross section within the columnar portion 130' and tapers to a four-sided pyramidal shaped within the tapered portion 130". FIG. 2C illustrates a perspective view of columnar-shaped positive NFC structure 130, according to another example. As illustrated, the NFC structure 130 of FIG. 2C comprises a columnar portion 130' having a generally circular cross section that tapers to a sharp tip 134 in the conical tapered portion 130".

The NFC structure 130, whether tapered or columnar, generally has a long narrow profile that extends up from the base 136. In particular, the NFC structure 130 may be greater than about 5 times as long as it is wide (or thick), according to some examples. In some examples, the NFC structure 130 may be five to ten times as long as it is wide. For example, the NFC structure 130 may have a width between several nanometers (nm) and about 100 nm and a length that is between about 500 nm and about 1 micron (μm).

In some examples, the surfaces 120 of the plurality of NFC structures 130 are surfaces of ridges (not illustrated) that have substantially sharp peaks or tips. In other words, the NFC structures 130 of the plurality may be or appear NFC structure-shaped only in cross section, according to some examples. For example, the NFC structures 130 illustrated in FIGS. 1A and 1B may be interpreted as ridges that are depicted or 'viewed' in a cross section that is taken substantially perpendicular to a direction that is parallel peaks of the ridges. NFC structures 130, such as those illustrated in FIG. 2A-2C may be considered 'three-dimensional' (3-D) NFC structures while NFC structures 130 that are ridges with substantially sharp peaks or valleys (depending on whether it is a positive or negative NFC structure) may be considered 'two dimensional' (2-D) NFC structures 130. As such, a plurality of ridges that, when viewed in cross section, appears substantially indistinguishable from a plurality of 3-D NFC structures is a 'plurality of NFC structures 130', by definition herein.

Figure 2D:
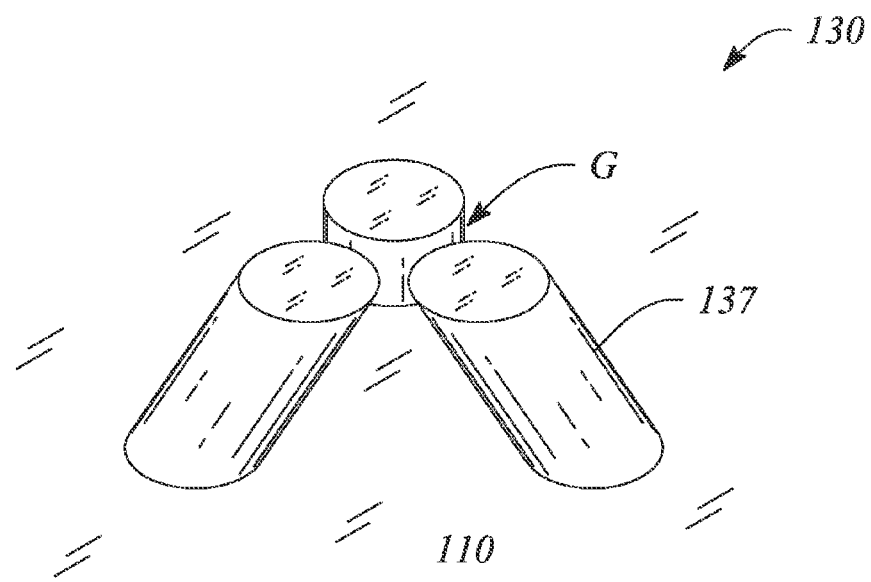
FIG. 2D illustrates a perspective view of an NFC structure, according to another example.

FIG. 2D illustrates a perspective view of an NFC structure 130, according to another example. In particular, the NFC structure 130 illustrated in FIG. 2D comprises a grouping of three nanofingers 137 that angle toward one another to define a gap G between the ends of the nanofingers at the tip 134. While illustrated with three nanofingers by way of example, in the NFC structure 130 comprising a grouping of angled nanofingers 137 may have 2, 3, 4, 5, 6 or more nanofingers 137.

Figure 2E:
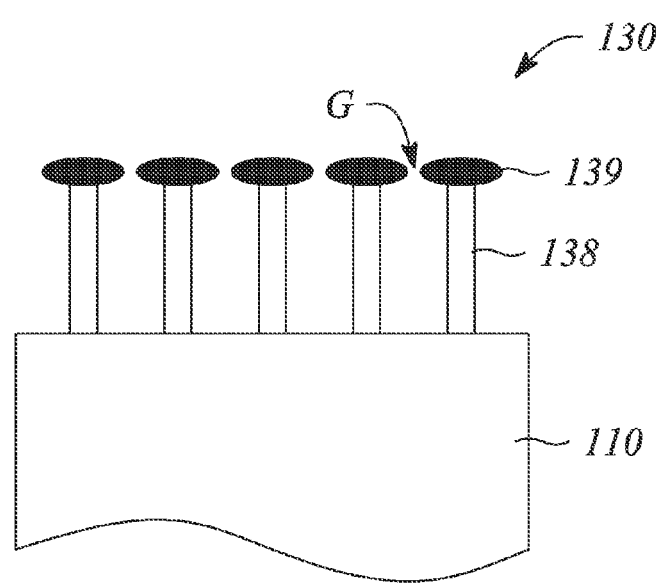
FIG. 2E illustrates a side view of an NFC structure, according to yet another example.

FIG. 2E illustrates a side view of an NFC structure 130, according to yet another example. In particular, the NFC structure 130 illustrated in FIG. 2E comprises a plurality of columnar elements 138 each of which have a cap 139 on an end corresponding to the tip 134 of the NFC structure 130. More particularly, the NFC structure 130 comprises at least two adjacent columnar elements 138 with respective caps 139 that are separated by a nanoscale gap G. The nanoscale gap G is configured to enhance or concentrate an incident electromagnetic field, as was discussed above. In some examples, the cap 139 comprises a metal and is termed a metallic cap 139. The surfaces 120 of the NFC structure 130 illustrated in FIG. 2E may be surfaces of the cap 139, for example.

In some examples, the plurality of NFC structures 130 may be formed into or from a material of the optical fiber 110. For example, when a core of the optical fiber 110 comprises PMMA, the plurality of NFC structures 130 may be formed into the PMMA using nanoimprint lithography. According to nanoimprint lithography, the optical fiber 110 may be heated to soften the material (e.g., PMMA) of the optical fiber 110. After the optical fiber core material is softened, a mold may be pressed into the terminal end 114. A shape of the mold is transferred to the optical fiber material to define or form the plurality of NFC structures 130. In another example, a mask may be place over the terminal end 114 of the optical fiber 110. One or both of wet or dry etching may be then employed to form the plurality of NFC structures 130 from the optical fiber core material.

In other examples, the plurality of NFC structures 130 may be formed from or in a layer of material deposited on the interface surface of or otherwise affixed adjacent to the terminal end 114 of the optical fiber 110. For example, the plurality of NFC structures 130 may be formed from a material (e.g., by nanoimprint lithography or by etching) and then transferred to the terminal end 114 of the optical fiber 110. In some of these examples, the plurality of NFC structures 130 may comprise a material that is substantially similar to a material of the core of the optical fiber 110. For example, the plurality of NFC structures 130 may be formed in a sheet of PMMA that is then transferred onto and affixed to the terminal end 114 of the optical fiber 110. In another example, PMMA may be printed onto the terminal end 114 of the optical fiber 110 in liquid form (e.g., using an inkjet printer or by depositing through a mask).

In other examples, a material of the NFC structures 130 may differ from a material of the optical fiber core. For example, the plurality of NFC structures 130 may comprise a semiconductor that is deposited on or otherwise affixed to the terminal end 114 of the optical fiber 110. The semiconductor may comprise silicon (Si) or germanium (Ge) or an alloy of Si and Ge, for example. In other examples, the semiconductor may comprise gallium arsenide (GaAs), indium gallium arsenide (InGaAs), and gallium nitride (GaN), as well as various other III-V, II-VI, and IV-VI compound semiconductors. In some of these examples, the semiconductor may be doped to render the semiconductor more conductive than an intrinsic or undoped form of the semiconductor. For example, the Si may be doped with phosphorus (P), an n-type dopant, or boron (B), a p-type dopant, to increase the conductivity. In another example, the plurality of NFC structures 130 may comprise a plastic film that is deposited on or otherwise affixed to the terminal end of either a POF or a glass optical fiber 110.

Referring back to FIGS. 1A and 1B, the SERS probe 100 further comprises nanoparticles 140 on the surfaces 120 of the NFC structures 130. The nanoparticles 140 provide surface enhanced Raman scattering by the analyte 102. The nanoparticles 140 comprise a Raman-active material. According to some examples, the nanoparticles 140 comprise metal and thus are metal nanoparticles. By definition herein, a Raman-active material is a material that facilitates Raman scattering and the production or emission of the Raman signal from an analyte adsorbed on or in a vicinity of a surface layer of the Raman-active material during Raman spectroscopy. Examples of Raman-active materials include, but are not limited to, gold (Au), silver (Ag), and copper (Cu). Various metals other than gold (Au) and silver (Ag) may also be Raman-active. In some examples, the Raman-active materials comprise a layer or layers having nanoscale surface roughness. Nanoscale surface roughness is generally characterized by nanoscale surface features on the surface of the layer(s). Nanoscale surface roughness may be produced spontaneously during deposition of the Raman-active material layer(s) (e.g., gold deposition), for example.

In particular, the surfaces 120 of the plurality of NFC structures 130, or at least a portion thereof, are coated with a layer of Raman-active material that comprises the nanoparticles 140. For example, the NFC structures 130 may be coated with a layer of metal such as, but not limited to, gold (Au), silver (Ag) or copper (Cu). The layer of Raman-active material may self-aggregate to produce the nanoparticles 140, for example. In another example, the layer comprises preformed nanoparticles of the Raman-active material that are deposited onto the surface 120 (e.g., by spraying or dipping). The layer(s) of nanoparticles may provide a nanoscale roughness that enhances Raman scattering, for example. In some examples, the layer of Raman-active material comprising the nanoparticles 140 is relatively thin compared to a width or thickness of the NFC structures 130. For example, the Raman-active material layer comprising the nanoparticles 140 may have a thickness that is less than about ½ of the width of the NFC structures 130. The Raman-active material layer comprising the nanoparticles may be approximately 5-100 nm thick, for example. For example, the nanoparticles 140 that coat the surfaces 120 may comprise a monolayer of gold (Au) nanoparticles 140 having diameters between about 10 nm and 100 nm, for example.

In some examples, the nanoparticles 140 may be substantially confined to or localized in a vicinity of the tip 134 of the NFC structures 130, as illustrated in FIG. 1A. In other examples, the nanoparticles 140 as part of the Raman-active layer may extend along more of the surfaces 120 of plurality of NFC structures 130 than just a vicinity of the tip 134. In some examples, an entire length of the NFC structure surfaces 120 is coated with the nanoparticles 140.

In some examples, the surfaces 120 of the plurality of NFC structures 130 may be functionalized to facilitate adsorption of the analyte 102. For example, the surfaces 120 in a vicinity of the tip 134 may be functionalized with a binding group to facilitate binding with a specific target analyte species. The binding group may provide one or more of hydroxyl, carboxyl, amine or amide binding moieties, for example. The functionalized surface may selectively bond with DNA or RNA, for example.

Figure 3:
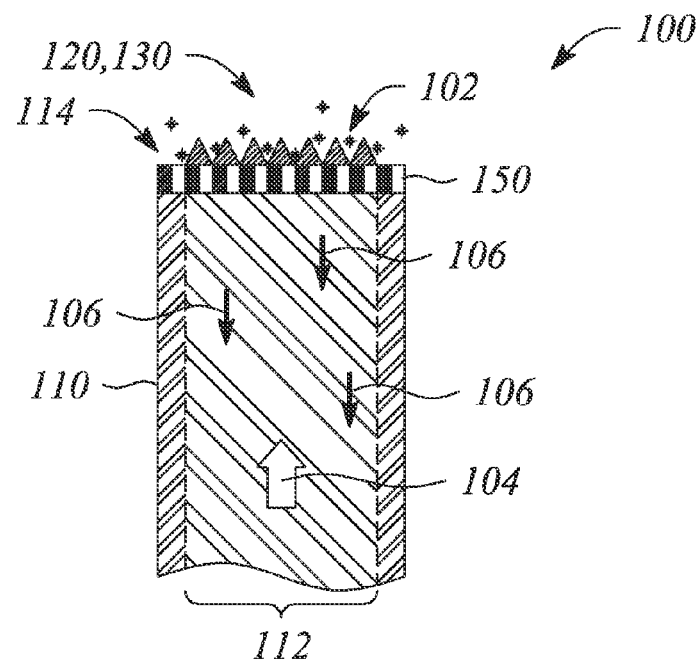
FIG. 3 illustrates a cross sectional view of a SERS probe apparatus, according to another example.

FIG. 3 illustrates a cross sectional view of a SERS probe apparatus 100, according to another example. In particular, as illustrated in FIG. 3, the SERS probe apparatus 100 further comprises a grating 150 between the terminal end 114 of the optical fiber 110 and the plurality of NFC structures 130. As such, the NFC structures 130 are indirectly contacted with the terminal end 114 (or interface surface thereof). The grating 150 may one or both of selectively collect and guide into the optical path 112 of the optical fiber 110 a Raman signal emitted by the analyte 102 as a result of the surface enhanced Raman scattering. Additionally, the grating 150 may provide further enhancement of one or both of Raman signal excitation and Raman signal collection.

For example, the grating 150 may provide an angle of acceptance of light directed into the optical path 112 of the optical fiber 110 that corresponds with an extent of the plurality of NFC structures 130 on the terminal end 114. The angle of acceptance may increase a portion of the emitted Raman signal 106 that is collected and guided by the optical fiber 110 when compared to the SERS probe apparatus 100 without the grating 150, for example. In another example, the grating 150 may provide filtering of optical signals. The filtering may have or provide a passband that selectively corresponds with a frequency or frequency range of the Raman scattering, for example. In yet another example, the grating 150 may provide both an angle of acceptance and filtering that are both substantially tuned to operate cooperatively with the Raman scattering from the analyte 102. As such, the grating 150 may substantially screen out optical signals not originating as Raman signals emitted by the analyte 102 while simultaneously increasing collection of the emitted Raman signals 106 by the optical fiber 110. Thus, the grating 150 may enhance a signal-to-noise ratio (SNR) of the Raman signal 106.

According to some examples, the optical fiber 110 guides within the optical path 112 both of the Raman signal 106 emitted by the analyte 102 as a result of the surface enhanced Raman scattering and an illumination signal 104 used to illuminate the nanoparticles and induce the surface enhanced Raman scattering. In particular, the illumination signal 104 may be guided to the plurality of NFC structures 130 along the optical path 112. The illumination signal 104 may then illuminate the analyte 102 to induce the analyte 102 to emit the Raman signal 106, for example, by surface enhanced Raman scattering. The emitted Raman signal 106 may then be collected by and guided away from the plurality of NFC structures 130 at the terminal end 114 along the optical path 112. As such, the optical fiber 110 provides a path 112 for both providing the illumination signal 104 that illuminates the analyte 102 to induce emission of the Raman signal 106 and receiving and guiding the emitted Raman signal 106 for the SERS probe apparatus 100, according to some examples. FIG. 3 further illustrates an example of the optical fiber 110 of the SERS probe apparatus 100 that both provides the illumination signal 104 and collects and guides the Raman signal 106 emitted by the analyte 102, according to an example. The illumination signal 104 and the Raman signal 106 are illustrated as arrows by way of example.

According to other examples, the illumination signal 104 is provided by another means and the optical fiber 110 is responsible for guiding the emitted Raman signal 106. For example, an illumination source (not illustrated) external to the SERS probe apparatus 100 may be positioned in a vicinity of the terminal end 114. The external illumination source may comprise a laser, for example, to provide the illumination signal 104 directed at the NFC structures 130 on the terminal end 114 of the optical fiber 110. In such examples, the optical fiber 110 may be responsible for collecting and guiding the emitted Raman signal 106 while the illumination signal 104 is provided by the external illumination source.

In some examples, the SERS probe apparatus 100 may comprise another optical fiber to provide the illumination signal 104. In these examples, the other optical fiber may be located adjacent to the optical fiber 110 and is configured to guide the illumination signal 104 within an optical path of the other optical fiber. Further, the other optical fiber may preferentially direct the illumination signal 104 toward the NFC structures 130 to illuminate the analyte 102.

Figure 4:
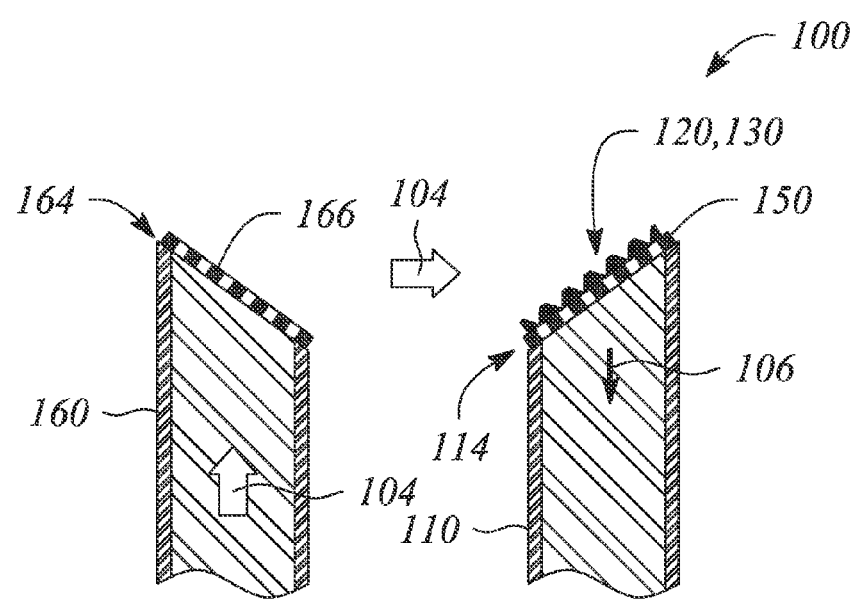
FIG. 4 illustrates a cross sectional view of a SERS probe apparatus having another optical fiber, according to an example.

FIG. 4 illustrates a SERS probe apparatus 100 having another optical fiber 160, according to an example. As illustrated, a terminal end 164 of the other optical fiber 160 is angled such that the illumination signal 104 is directed (e.g., by refraction) in the direction of the optical fiber 110 and the surfaces 120 of the NFC structures 130 at a terminal end 114 of the optical fiber 110. In some examples, the terminal end 164 of the other optical fiber 160 may further comprise one or both of a structure or a shape that facilitates directing the illumination signal 104. For example, the terminal end 164 may be lens shaped to focus the illumination signal 104 on the NFC structures 130. In some examples, the structure on the terminal end 164 of the other optical fiber 160 may further comprise a grating 166. The grating 166 may direct the illumination signal 104 toward the NFC structures 130, as illustrated in FIG. 4. In FIG. 4, the optical fiber 110 is also equipped with a grating 150, by way of example.

Figure 5:
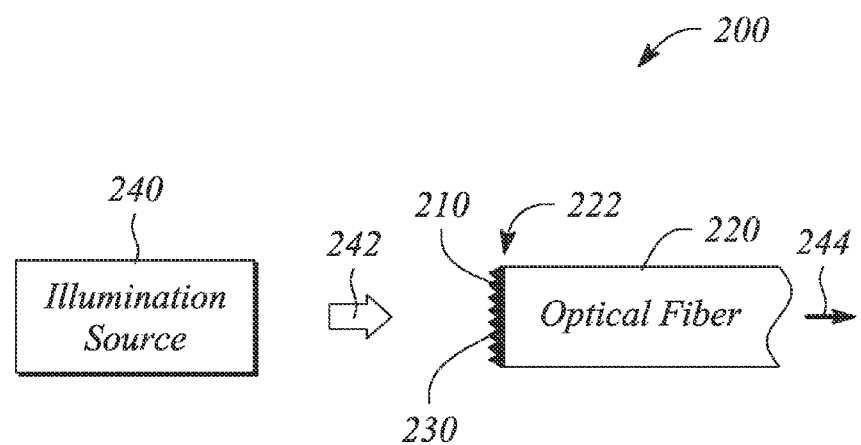
FIG. 5 illustrates a block diagram of a SERS probe system, according to an example.

FIG. 5 illustrates a block diagram of a SERS probe system 200, according to an example. As illustrated, the SERS probe system 200 comprises surfaces of a plurality of nanoscale field concentrator (NFC) structures 210. The NFC structures 210 are adjacent to a terminal end 222 of an optical fiber 220. The terminal end 222 intersects an optical path of the optical fiber 220. In some examples, the optical fiber 220 may be substantially similar to the optical fiber 110 described above with respect to the SERS probe apparatus 100. Further, according to some examples, the surfaces and NFC structures 210 of the plurality may be substantially similar to respective surfaces 120 and NFC structures 130 described above with respect to the SERS probe apparatus 100, according to some examples.

In particular, in some examples, the NFC structures 210 are positive NFC structures while in other examples the NFC structures 210 are negative NFC structures. In some examples, the NFC structures 210 are integral with and formed into a material of the optical fiber 220. In other examples, the NFC structures 210 are formed from a material that is applied to the optical fiber 220.

The SERS probe system 200 further comprises metal nanoparticles 230. The metal nanoparticles 230 are on the surfaces of the NFC structure 210 plurality. In some examples, the metal nanoparticles 230 are substantially similar to the nanoparticles 140 described above with respect to the SERS probe apparatus 100. Moreover, according to some examples, the SERS probe system 200 comprises the SERS probe apparatus 100.

The SERS probe system 200 further comprises an illumination source 240. The illumination source 240 provides an illumination signal 242. The illumination signal 242 illuminates the metal nanoparticles 230 to induce a Raman scattered signal 244 from an analyte in the presence of the metal nanoparticles 230. In some examples, the illumination signal 242 is substantially similar to the illumination signal 104 described above with respect to the SERS probe apparatus 100. In some examples, the Raman scattered signal 244 is substantially similar to the Raman signal 106 described above with respect to the SERS probe apparatus 100.

In some examples (not illustrated), the optical path of the optical fiber 220 both collects and then guides the Raman scattered signal 244 away from the terminal end 222 of the optical fiber 220 and further guides the illumination signal 242 of the illumination source 240 to the terminal end 222 of the optical fiber 220 (e.g., similar to the example illustrated in FIG. 3). In other examples, the illumination signal 242 is provided to the NFC structures 210 by another optical path of another optical fiber (e.g., a direct illumination or via another optical fiber, which may be similar to the example illustrated in FIG. 4, for example).

Figure 6:
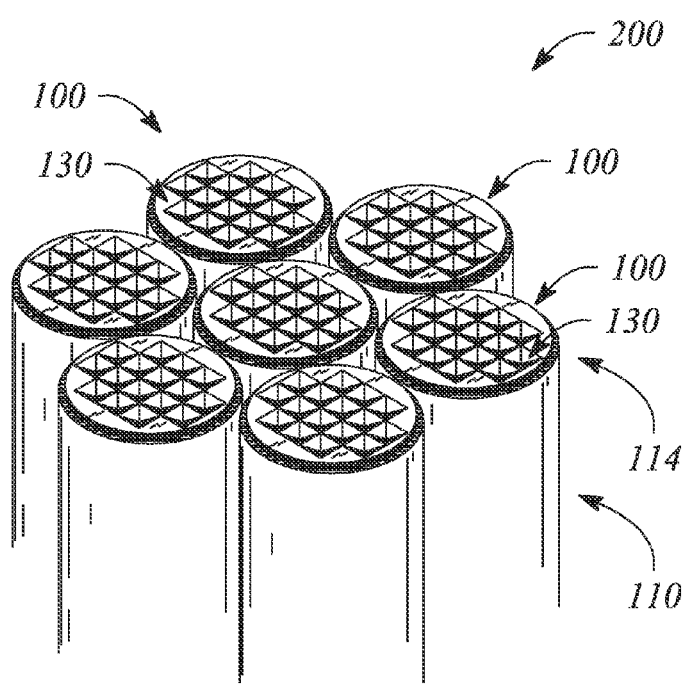
FIG. 6 illustrates a perspective view of a SERS probe system, according to another example.

FIG. 6 illustrates a perspective view of a SERS probe system 200, according to another example. As illustrated, the SERS probe system 200 comprises a plurality of SERS probe apparatuses 100. The plurality of SERS probe apparatuses 100 are bundled together, as illustrated. In some examples, the SERS probe apparatuses 100 each preferentially produce and collect different Raman scattered signals. For example, each of the SERS probe apparatuses 100 may filter (e.g., using a grating) specific wavelengths of the Raman scattered signal. In another example, a different wavelength illumination signal may be delivered to the NFC structures 130 on the terminal ends 114 of optical fibers 110 of each of the SERS probe apparatuses 100 of the plurality. In yet other examples, characteristics of one or more of the NFC structures 130, the metal nanoparticles, a grating on the terminal end 114, and a functionalization of the NFC structures 130 of different ones of the SERS probe apparatuses 100 of the plurality may be tuned or may differ. Each of these examples may allow the SERS probe apparatuses 100 to operate in concert with one another and to provide one or both of parallel detection of adsorbed analytes and demultiplexing of Raman scattered signals produced by one or more analytes as a result of the surface enhanced Raman scattering.

Figure 7:
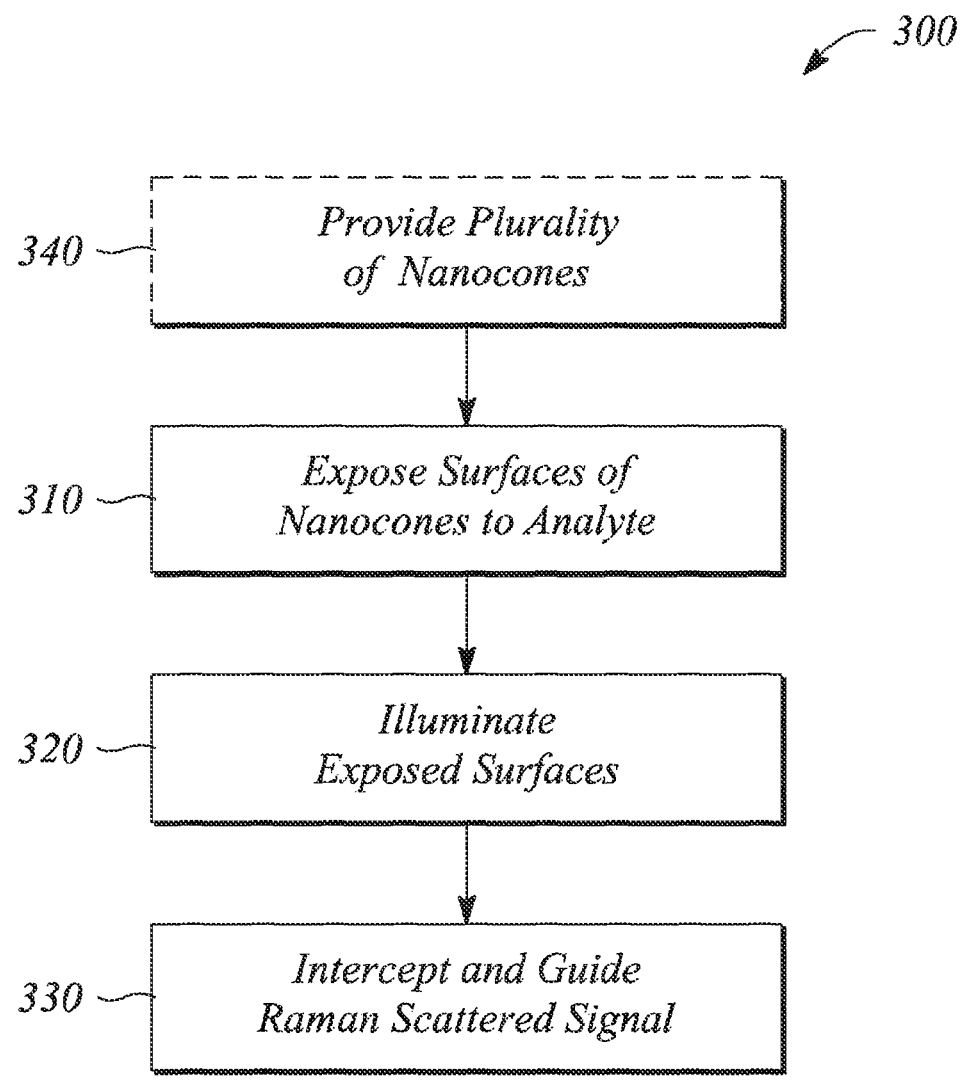
FIG. 7 illustrates a flow chart of a method of surface enhanced Raman spectroscopy (SERS) probing, according to an example.

FIG. 7 illustrates a flow chart of a method 300 of surface enhanced Raman spectroscopy (SERS) probing, according to an example. As illustrated, the method 300 of SERS probing comprises exposing 310 surfaces of a plurality of nanoscale field concentrator (NFC) structures to an analyte. The surfaces are coated with nanoparticles and the plurality of NFC structures is adjacent to a terminal end of an optical fiber, for example in either direct contact or indirect contact with the terminal end. According to some examples, the surfaces, NFC structures, nanoparticles and optical fiber are substantially similar to respective ones of the surfaces 120, the NFC structures 130, the nanoparticles 140 and the optical fiber 110, described above with respect to the SERS probe apparatus 100.

The method 300 of SERS probing further comprises illuminating 320 the surfaces exposed 310 to the analyte with an illumination signal to induce Raman scattering from the analyte. The Raman scattering produces a Raman scattered signal. According to some examples, the analyte, the illumination signal and the Raman scattered signal may be substantially similar to the analyte 102, the illumination signal 104 and the Raman signal 106, respectively, that are described above with respect to the SERS probe apparatus 100. In particular, according to some examples, illuminating 320 the exposed 310 surfaces comprises conducting the illumination signal along the optical path of the optical fiber. In other examples, illuminating 320 may comprise externally providing the illumination signal (e.g., via another optical fiber or an external optical source).

The method 300 of SERS probing further comprises intercepting and guiding 330 a portion of the Raman scattered signal using the optical fiber. According to some examples, the intercepted and guided 330 portion of the Raman scattered signal is conducted away from the terminal end of the optical fiber within the optical path of the optical fiber. The intercepted and guided 330 portion of the Raman scattered signal may be conducted to a detector, for example.

According to some examples, the method 300 of SERS probing may further comprise providing 340 the plurality of NFC structures adjacent to the terminal end of the optical fiber. Providing 340 the plurality of NFC structures is illustrated in FIG. 7 using a dashed line indicating that the plurality of NFC structures may be provided 340 in some examples. In some examples, the NFC structures are provided 340 by forming NFC structures in a material of the optical fiber at the terminal end. For example, providing 340 the plurality of NFC structures may comprise applying imprint lithography to the terminal end of the optical fiber. The imprint lithography forms the NFC structures directly into a material (e.g., PMMA) of the optical fiber at the terminal end of the optical fiber. In another example, the NFC structures may be formed into the optical fiber material using another lithographic process such as, but not limited to, wet etching and dry etching. In other examples, the NFC structures are provided 340 by another means such as, but not limited to, applying preformed NFC structures to the terminal end of the optical fiber, or forming (e.g., by etching or printing) a material that has been applied to the terminal end of the optical fiber into NFC structures, for example. The material applied to the terminal end may be the material substantially similar to the optical fiber material or another material (e.g., glass, silicon, etc.) that differs from the optical fiber material, according to various examples. According to some examples, a forming method including, but not limited to, etching (e.g., one or both of dry etching and wet etching) and imprint lithography may be used to form the applied material into the NFC structures. In another example, the NFC structures may be provided 340 comprising forming the NFC structures as the material is applied to the terminal end of the fiber optic. For example, the NFC structures may be applied and formed by methods including, but not limited to, growing (e.g., by vapor-liquid-solid growth) the NFC structures on the terminal end of the optical fiber, and printing the NFC structures onto the terminal end of the optical fiber.

Thus, there have been described examples of a surface enhanced Raman spectroscopy (SERS) probe apparatus and SERS probe system as well as a method of SERS probing that employ surfaces of a plurality of NFC structures on a terminal end of an optical fiber. It should be understood that the above-described examples are merely illustrative of some of the many specific examples that represent the principles of what is claimed. Clearly, those skilled in the art can readily devise numerous other arrangements without departing from the scope defined by the following claims.

What is claimed is:

1. A surface enhanced Raman spectroscopy (SERS) probe apparatus comprising:
a single optical fiber having an optical path and a terminal end that terminates the optical path;
a plurality of nanoscale field concentrator (NFC) structures at the terminal end of the single optical fiber, first ends of all of the NFC structures of the plurality being adjacent to the terminal end of the single optical fiber; and
nanoparticles on surfaces of of each of the NFC structures, the nanoparticles being Raman-active to an analyte.

2. The SERS probe apparatus of claim 1, wherein the NFC structures of the plurality are negative NFC structures.

3. The SERS probe apparatus of claim 1, wherein the NFC structures of the plurality comprise a material of the terminal end of the optical fiber.

4. The SERS probe apparatus of claim 1, further comprising a grating between the terminal end of the optical fiber and the plurality of NFC structures, the grating being selective for a Raman signal of the analyte.

5. The SERS probe apparatus of claim 1, wherein the optical fiber supports both a Raman signal and an illumination signal along the optical path.

6. The SERS probe apparatus of claim 1, further comprising another optical fiber having a terminal end adjacent to second ends of the plurality of NFC structures, the second ends being opposite the first ends, wherein the other optical fiber supports an illumination signal to illuminate the nanoparticles.

7. A SERS probe system comprising the SERS probe apparatus of claim 1, the SERS probe system further comprising a plurality of other SERS probe apparatuses to operate in concert with one another and to provide one or both of parallel detection of adsorbed analytes and demultiplexing of Raman signals produced by one or more analytes as a result of the surface enhanced Raman scattering.

8. The SERS probe apparatus of claim 1, wherein the NFC structure comprises a grouping of a plurality of nanofingers, each nanofinger of the grouping being angled toward an adjacent nanofinger of the grouping at second ends of the NFC structure opposite the first end, wherein ends of the nanofingers at the second end of the NFC structure are separated from one another by a nanoscale gap.

9. A surface enhanced Raman spectroscopy (SERS) probe system comprising:
a plurality of nanoscale field concentrator (NFC) structures, the plurality of NFC structures being adjacent to a terminal end of a single optical fiber, the terminal end intersecting an optical path of the single optical fiber;
metal nanoparticles on surfaces of each NFC structure of the plurality; and
an illumination source to illuminate the metal nanoparticles.

10. The SERS probe system of claim 9, wherein the NFC structures of the plurality are positive NFC structures integral with and formed into a material of the optical fiber.

11. The SERS probe system of claim 9, wherein the optical path of the optical fiber is configured to both collect and guide the Raman scattered signal away from the terminal end of the optical fiber, the optical path further being configured to guide an illumination signal of the illumination source to the terminal end of the optical fiber.

12. A method of surface enhanced Raman spectroscopy (SERS) probing, the method comprising:
exposing surfaces of a plurality of nanoscale field concentrator (NFC) structures to an analyte, the surfaces being coated with nanoparticles, the plurality of NFC structures being adjacent to a terminal end of a same optical fiber, the terminal end intersecting an optical path of the optical fiber;
illuminating the surfaces exposed to the analyte with an illumination signal to induce surface enhanced Raman scattering from the analyte, the surface enhanced Raman scattering producing a Raman scattered signal; and
intercepting and guiding a portion of the Raman scattered signal using the same optical fiber, the intercepted and guided portion of the Raman scattered signal being conducted away from the terminal end of the optical fiber within an optical path of the same optical fiber.

13. The method of SERS probing of claim 12, further comprising providing the plurality of NFC structures adjacent to the terminal end of the optical fiber, the provided NFC structures having sharp tips.

14. The method of SERS probing of claim 13, wherein providing the plurality of NFC structures comprises applying imprint lithography to the terminal end of the optical fiber, the imprint lithography forming the NFC structures into a material of the optical fiber at the terminal end.

15. The method of SERS probing of claim 12, wherein illuminating the surfaces comprises guiding the illumination signal along the optical path of the optical fiber to induce the surface enhanced Raman scattering from the analyte.

* * * * *

UNITED STATES PATENT AND TRADEMARK OFFICE
CERTIFICATE OF CORRECTION

| | | |
|---|---|---|
| PATENT NO. | : 9,001,324 B2 | Page 1 of 1 |
| APPLICATION NO. | : 13/810982 | |
| DATED | : April 7, 2015 | |
| INVENTOR(S) | : Zhiyong Li et al. | |

It is certified that error appears in the above-identified patent and that said Letters Patent is hereby corrected as shown below:

In the Claims

In column 13, line 57, in Claim 1, delete "of of" and insert -- of --, therefor.

Signed and Sealed this
First Day of December, 2015

Michelle K. Lee
*Director of the United States Patent and Trademark Office*